US009763861B2

(12) United States Patent
Lei et al.

(10) Patent No.: US 9,763,861 B2
(45) Date of Patent: *Sep. 19, 2017

(54) STABLE, FLOWABLE SILICA CAPSULE FORMULATION

(71) Applicant: International Flavors & Fragrances Inc., New York, NY (US)

(72) Inventors: Yabin Lei, Holmdel, NJ (US); Li Xu, Newark, NJ (US); Carol Joyce, Toms River, NJ (US)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 40 days.

This patent is subject to a terminal disclaimer.

(21) Appl. No.: 14/057,083

(22) Filed: Oct. 18, 2013

(65) Prior Publication Data
US 2014/0044760 A1 Feb. 13, 2014

Related U.S. Application Data

(63) Continuation-in-part of application No. 13/422,090, filed on Mar. 16, 2012, which is a continuation-in-part of application No. 12/793,911, filed on Jun. 4, 2010, now Pat. No. 9,044,732, which is a continuation-in-part of application No. 12/328,340, filed on Dec. 4, 2008, now abandoned.

(60) Provisional application No. 61/453,977, filed on Mar. 18, 2011.

(51) Int. Cl.
| *A61K 8/25* | (2006.01) |
| *A61Q 5/00* | (2006.01) |
| *A61Q 5/02* | (2006.01) |
| *A61Q 11/00* | (2006.01) |
| *A61Q 15/00* | (2006.01) |
| *A61Q 19/10* | (2006.01) |
| *C11D 3/16* | (2006.01) |
| *B01J 13/18* | (2006.01) |
| *B01J 13/20* | (2006.01) |
| *C11D 3/50* | (2006.01) |
| *C11D 17/00* | (2006.01) |
| *A61K 8/11* | (2006.01) |
| *A61Q 13/00* | (2006.01) |
| *A61Q 5/12* | (2006.01) |

(52) U.S. Cl.
CPC ................ *A61K 8/25* (2013.01); *A61K 8/11* (2013.01); *A61Q 5/00* (2013.01); *A61Q 13/00* (2013.01); *A61Q 15/00* (2013.01); *B01J 13/18* (2013.01); *B01J 13/206* (2013.01); *C11D 3/162* (2013.01); *C11D 3/505* (2013.01); *C11D 17/0039* (2013.01); *A61K 2800/412* (2013.01); *A61K 2800/56* (2013.01); *A61Q 5/02* (2013.01); *A61Q 5/12* (2013.01); *A61Q 11/00* (2013.01); *A61Q 19/10* (2013.01)

(58) Field of Classification Search
None
See application file for complete search history.

(56) References Cited

U.S. PATENT DOCUMENTS

| 4,081,384 A | 3/1978 | Pracht ........................... 510/523 |
| 4,234,627 A | 11/1980 | Schilling .......................... 8/137 |
| 4,605,554 A * | 8/1986 | Prussin et al. .................. 424/66 |
| 5,112,688 A | 5/1992 | Michael ..................... 428/402.2 |
| 5,145,842 A | 9/1992 | Driedger et al. ............... 514/63 |
| 5,176,903 A | 1/1993 | Goldberg et al. |
| 5,492,870 A | 2/1996 | Wilcox et al. ................... 501/80 |
| 6,194,375 B1 | 2/2001 | Ness et al. ........................ 512/4 |
| 6,238,650 B1 | 5/2001 | Lapidot et al. ................. 424/59 |
| 6,248,703 B1 | 6/2001 | Finucane et al. ............. 510/152 |
| 6,303,149 B1 | 10/2001 | Magdassi et al. ............ 424/489 |
| 6,329,057 B1 | 12/2001 | Dungworth et al. ......... 428/403 |
| 6,337,089 B1 | 1/2002 | Yoshioka et al. ............. 424/451 |
| 6,537,583 B1 | 3/2003 | Dupuis et al. |
| 6,855,335 B2 | 2/2005 | Seok et al. ..................... 424/489 |
| 7,112,339 B1 | 9/2006 | Ahola et al. |
| 7,147,915 B2 | 12/2006 | Kawai et al. ............... 428/402.2 |
| 7,758,888 B2 | 7/2010 | Lapidot et al. ............... 424/489 |
| 2002/0064541 A1 | 5/2002 | Lapidot et al. ............... 424/401 |
| 2003/0082276 A1 | 5/2003 | Subramaniam et al. |
| 2004/0175404 A1 | 9/2004 | Shefer et al. |
| 2004/0256748 A1 | 12/2004 | Seok et al. |
| 2005/0153135 A1 | 7/2005 | Popplewell et al. |
| 2005/0265938 A1 | 12/2005 | Cohen et al. |
| 2007/0051274 A1 | 3/2007 | Saito et al. ................. 106/287.1 |

(Continued)

FOREIGN PATENT DOCUMENTS

| DE | WO 2011124706 A1 * | 10/2011 | ........... A23L 1/0029 |
| EP | 0478326 A1 | 4/1992 | |

(Continued)

OTHER PUBLICATIONS

Larsson et al., Annual Transactions of the Nordic Rheology Society, vol. 20 (2012).*
Flick, E.W. "An Industrial Guide" *Cosmetic Additives* Park Ridge, New Jersey: Noyes Publications, 1991 p. 194.
O'Sullivan et al. "Silica-Shell/Oil-Core Microcapsules with Controlled Shell Thickness and Their Breakage Stress" Langmuir 2009 25(14):7962-7966.
Office Communication dated Mar. 15, 2012 from U.S. Appl. No. 12/328,340, filed Dec. 4, 2008.
Office Communication dated Oct. 16, 2012 from U.S. Appl. No. 12/793,911, filed Jun. 4, 2010.
Office Communication dated May 9, 2013 from U.S. Appl. No. 12/793,911, filed Jun. 4, 2010.

(Continued)

*Primary Examiner* — Bethany Barham
*Assistant Examiner* — Lisbeth C Robinson
(74) *Attorney, Agent, or Firm* — Martin Zhang; XuFan Tseng; Elizabeth M Stover

(57) ABSTRACT

A flowable, stable silica capsule formulation composed of a silica capsule suspension and an adjuvant for use in a personal care product, a beauty care product, a fabric care product, a home care product, a personal hygiene product, an oral care product is provided.

18 Claims, 1 Drawing Sheet

(56) References Cited

U.S. PATENT DOCUMENTS

| | | |
|---|---|---|
| 2007/0078071 A1 | 4/2007 | Lee et al. |
| 2007/0190325 A1 | 8/2007 | Berg-Schultz et al. |
| 2007/0227398 A1 | 10/2007 | Lee et al. |
| 2008/0317795 A1* | 12/2008 | Traynor et al. ............ 424/401 |
| 2009/0004418 A1 | 1/2009 | Takaki et al. ............ 428/36.92 |
| 2009/0025361 A1 | 1/2009 | Blase et al. |
| 2009/0047230 A1 | 2/2009 | Caballero et al. |
| 2009/0246279 A1 | 10/2009 | Kong et al. ............ 424/486 |
| 2010/0143422 A1 | 6/2010 | Popplewell et al. |

FOREIGN PATENT DOCUMENTS

| | | |
|---|---|---|
| EP | 1627573 A1 | 2/2006 |
| EP | 2025364 A1 | 2/2009 |
| EP | 2196257 A2 | 6/2010 |
| EP | 2500087 A2 | 9/2012 |
| FR | 2703927 A1 | 10/1994 |
| FR | 2780901 A1 | 1/2000 |
| GB | 2416524 A | 2/2006 |
| WO | WO94/04260 | 3/1994 |
| WO | WO94/04261 | 3/1994 |
| WO | WO99/03450 | 1/1999 |
| WO | 00/09652 A2 | 2/2000 |
| WO | 2011003805 A2 | 1/2001 |
| WO | 03/034979 A2 | 5/2003 |
| WO | 03066209 A1 | 8/2003 |
| WO | 2005/009604 A1 | 2/2005 |
| WO | 2008144734 A1 | 11/2008 |
| WO | 2009106318 A2 | 9/2009 |
| WO | 2011161265 A2 | 12/2011 |
| WO | 2013092958 A1 | 6/2013 |

OTHER PUBLICATIONS

Office Communication dated Aug. 22, 2013 from U.S. Appl. No. 13/422,090, filed Mar. 16, 2012.

Mamoru Aizawa Aizawa et al. 2000. Preparation of Spherical Hydrous Silica Oxide Particles under Acidic Condition Sol-Gel Processing. Journal of Sol-Gel Science and Technology. 19:329-332.

European Search Report. EP14189284. International Flavors & Fragrances Inc. Feb. 2, 2015.

BASF publication, title: PVP and More . . . Luvitec, Luvicross and Clooacral Val versitle specialty polymers for technical application, download from http://www.micronal.de/portal/streameron Aug. 6, 2014, published Apr. 2009.

"Non-Defatting Body Wash", Cosmetic & Toiletry Formulations 2nd Ed. vol. 2, Flick, Ed. p. 99 (1992).

Hofer et al., Langmuir, 14: 4014-4020 (2001).

Extended European Search Report dated Sep. 25, 2015 from European Patent Office for Application No. 14189395.8, filed Oct. 17, 2014.

Extended European Search Report dated May 13, 2015 from European Patent Office for Application No. 12159991.4, filed Mar. 16, 2012.

* cited by examiner

SLURRY CONTROL     SLURRY + 0.5 % PQ-6

STABLE, FLOWABLE SILICA CAPSULE FORMULATION

INTRODUCTION

This application is a continuation-in-part of U.S. application Ser. No. 13/422,090, filed Mar. 16, 2012, which claims benefit of priority from U.S. Provisional Application Ser. No. 61/453,977, filed Mar. 18, 2011; and is a continuation-in-part of U.S. application Ser. No. 12/793,911, filed Jun. 4, 2010, which is continuation-in-part of U.S. application Ser. No. 12/328,340, filed Dec. 4, 2008, abandoned, the contents of which are incorporated herein by reference in their entireties.

BACKGROUND

Fragrance chemicals are used in numerous products to enhance the consumer's enjoyment of a product. Fragrance chemicals are added to consumer products such as laundry detergents, fabric softeners, soaps, detergents, personal care products, such as but not limited to shampoos, body washes, deodorants and the like, as well as numerous other products.

In order to enhance the effectiveness of the fragrance materials for the user, various technologies have been employed to enhance the delivery of the fragrance materials at the desired time. One widely used technology is encapsulation of the fragrance material in a protective coating. Frequently the protective coating is a polymeric material. The polymeric material is used to protect the fragrance material from evaporation, reaction, oxidation or otherwise dissipating prior to use. A brief overview of polymeric encapsulated fragrance materials is disclosed in U.S. Pat. No. 4,081,384, which describes a softener or anti-stat core coated by a polycondensate suitable for use in a fabric conditioner; U.S. Pat. No. 5,112,688, which discloses selected fragrance materials having the proper volatility to be coated by coacervation with micro particles in a wall that can be activated for use in fabric conditioning; U.S. Pat. No. 5,145,842, which describes a solid core of a fatty alcohol, ester, or other solid plus a fragrance coated by an aminoplast shell; and U.S. Pat. No. 6,248,703, which describes various agents including fragrance in an aminoplast shell that is included in an extruded bar soap.

While encapsulation of fragrance in a polymeric shell can help prevent fragrance degradation and loss, it is often not sufficient to significantly improve fragrance performance in consumer products. Therefore, methods of aiding the deposition of encapsulated fragrances have been described. U.S. Pat. No. 4,234,627 discloses a liquid fragrance coated with an aminoplast shell further coated by a water insoluble meltable cationic coating in order to improve the deposition of capsules from fabric conditioners. U.S. Pat. No. 6,194,375 discloses the use of hydrolyzed polyvinyl alcohol to aid deposition of fragrance-polymer particles from wash products. U.S. Pat. No. 6,329,057 discloses the use of materials having free hydroxy groups or pendant cationic groups to aid in the deposition of fragranced solid particles from consumer products.

In addition, the use of silica to form microcapsule formulations specifically designed to prevent an encapsulated active ingredient from leaving the microcapsule has been described. This is desirable when the active ingredient is an irritant to the body tissue to which it is applied. It is also is desired when the active ingredient acts by interaction with light, such as sunlight. However, U.S. Pat. No. 6,303,149 fails to disclose compositions and methods for releasing and hence delivering the active ingredients. Despite these and many other disclosures there is an ongoing need for the improved delivery of fragrance materials for various personal care products, rinse-off products and leave-on products that provide improved performance.

SUMMARY OF THE INVENTION

The present invention is a flowable, stable silica capsule formulation composed of a silica capsule suspension and an adjuvant. In one embodiment the silica capsule suspension includes core-shell capsules encapsulating an active material, e.g., a fragrance oil. In other embodiments, the adjuvant is a nonionic polymer (e.g., polyvinylpyrrolidone, polyvinyl alcohol, polyethylene glycol, polyethylene oxide, polyethylene oxide-polypropylene oxide, polyethylene oxide-polypropylene oxide-polyethylene oxide, or a combination thereof), cationic polymer (e.g., a polydiallyldimethylammonium chloride such as Polyquaterium-6, a vinyl pyrrolidone/dimethylaminoethyl methacrylate copolymer such as Polyquaternium-11, an acrylic acid/methacrylamidopropyl trimethyl ammonium chloride/methyl acrylate terpolymer such as Polyquaternium-47, or a combination thereof), anionic polymer (e.g., a polystyrene sulfonic acid, polyacrylic acid, hyaluronic acid, sodium alginate, sodium carboxymethylcellulose, or a combination thereof), anionic surfactant (e.g., sodium laureth sulfate, complex ester of phosphoric acid and ethoxylated cosmetic grade oleyl alcohol, or a combination thereof), or a combination thereof. In particular embodiments, the adjuvant is 0.01% to 5% of the formulation. In other embodiments, the polymeric (nonionic, cationic, or anionic) adjuvant has a molecular weight in the range of 15,000 to 3,000,000 or more preferably in the range of 50,000 to 1,500,000. In alternative embodiments, the adjuvant is added to the silica capsule suspension during or after the preparation of the silica capsule suspension.

A personal care product, (e.g., an aerosol antiperspirant, stick antiperspirant, roll-on antiperspirant, emulsion spray antiperspirant, clear emulsion stick antiperspirant, soft solid antiperspirant, emulsion roll-on antiperspirant, clear emulsion stick antiperspirant, opaque emulsion stick antiperspirant, clear gel antiperspirant, clear stick deodorant or spray deodorant, shampoo, hair conditioner, hair rinse, hair refresher, body wash, soap), a beauty care product (e.g., a fine fragrance or an Eau De Toilette product); fabric care product (e.g., a rinse conditioner, liquid detergent or powder detergent), home care product (e.g., an all-purpose cleaner or fabric refresher), personal hygiene product (e.g., hand sanitizer) or oral care product (e.g., tooth powder) containing the flowable, stable silica capsule formulation is also provided.

DETAILED DESCRIPTION OF THE INVENTION

It has been discovered that silica capsule formulations can be stabilized, yet remain flowable, when suspended in a solution containing an adjuvant. Given the stability of the formulation of the invention, storage of the silica capsules is increased thereby enhancing the utility of the silica capsules. The stabilized silica capsule formulations are suitable for a wide range of consumer applications including personal care products such as deodorants, antiperspirants, shampoos, conditioners and body washes; beauty care products such as fine fragrance and Eau De Toilette products; fabric care products such as rinse conditioners and liquid and powder detergents; home care products such as all-purpose cleaners and fabric refreshers; personal hygiene products such as hand sanitizers; and oral care products such as tooth powder.

Accordingly, the present invention is a silica gel capsule formulation composed of a silica capsule slurry or suspension and an adjuvant and a method of using the same to provide a stable, flowable capsule in a consumer product. In particular embodiments of the invention, the silica capsule suspension is composed of core-shell silica capsules that encapsulate an active material such as a fragrance oil, essential oil, plant extract or mixture thereof, as described herein. In certain embodiments, the silica capsule suspension is composed of core-shell silica capsules that encapsulate a fragrance.

Figure 1:
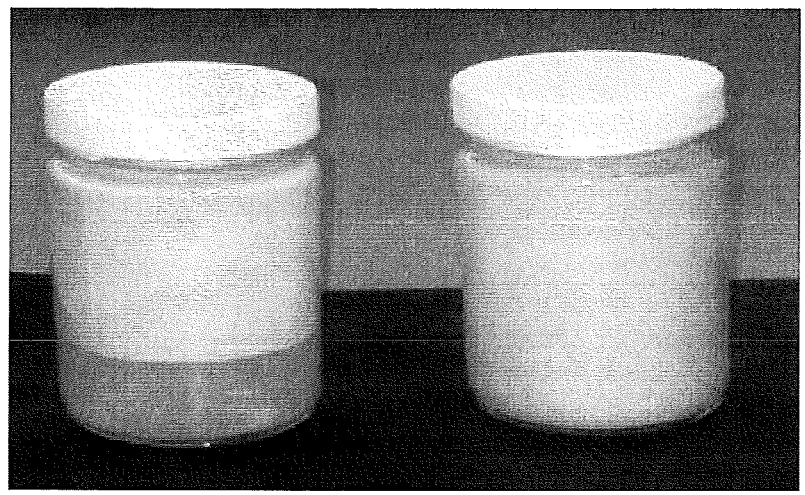
FIG. 1 showing the benefit of Polyquaterium-6 (PQ-6) as an adjuvant on the stability of a silica capsule fragrance capsule slurry.

In accordance with the method of the invention, a slurry or suspension of silica capsules is mixed with an adjuvant to form a stable, flowable capsule formulation. Subsequently, the mixture is incorporated into a consumer product base to obtain a consumer product. In some embodiments, the adjuvant is added with the silica capsules in process. In other embodiments, the adjuvant is added to the silica capsules after the capsules have been prepared and cured. A capsule formulation is considered stable if, after a period of time (e.g., 4-8 weeks) it has minimal or no separation and/or does not cream, foam or gel. For the purposes of the present invention, a stable silica capsule formulation is one with less than 30%, less than 20%, less than 10%, less than 5% or less than 1% separation as determined by measuring the proportion of the formulation where the silica capsules are in suspension compared to the proportion of the formulation without silica capsules. Such measurements can be made as depicted in FIG. 1.

Silica/Sol-Gel Capsules. Sol-gel precursors, i.e., starting compounds capable of forming gels, suitable for the purposes of the invention are known in the art. Sol-gel precursors usable in accordance with the invention are, for example, compounds that are capable of forming gels including, e.g., silicon, boron, aluminum, titanium, zinc, zirconium and vanadium. The precursors can also include metal alkoxides and diketonates. Sol-gel precursors suitable for the purposes of the invention are selected in particular from the group of di-, tri- and/or tetrafunctional silicic acid, boric acid and alumoesters, more particularly alkoxysilanes (alkyl orthosilicates), and precursors thereof. One example of sol-gel precursors suitable for the purposes of the invention are alkoxysilanes corresponding to the following general formula: $(R_1O)(R_2O)M(X)(X')$, wherein M is Si, Ti, or Zr; X is equal to hydrogen, or $-OR_3$; X' is equal to hydrogen, or $-OR_4$; and $R_1$, $R_2$, $R_3$ and $R_4$ independently represent an organic group, more particularly a linear or branched alkyl group, preferably a $C_{1-12}$ alkyl.

As indicated, the microcapsules of this invention can be prepared by conventional methods to encapsulate one or more active materials. In some embodiments, the active material is encapsulated by a polymer in the presence of a capsule formation aid, e.g., a surfactant or dispersant. Classes of protective colloid or emulsifier of use as surfactants or dispersants include maleic-vinyl copolymers such as the copolymers of vinyl ethers with maleic anhydride or acid, sodium lignosulfonates, maleic anhydride/styrene copolymers, ethylene/maleic anhydride copolymers, and copolymers of propylene oxide, ethylenediamine and ethylene oxide, polyvinylpyrrolidone, polyvinyl alcohols, carboxymethyl cellulose, fatty acid esters of polyoxyethylenated sorbitol and sodium dodecylsulfate.

Commercially available surfactants for use as capsule formation aids include, but are not limited to, sulfonated naphthalene-formaldehyde condensates such as MORWET D425 (Akzo Nobel); partially hydrolyzed polyvinyl alcohols such as MOWIOLs, e.g., MOWIOL 3-83 (Air Products); sulfonated polystyrenes such as FLEXAN II (Akzo Nobel).

Adjuvants. In accordance with the present invention, the stability of freshly cured silica capsules is enhanced by the inclusion of an adjuvant. As is known in the chemical arts, an adjuvant is a material added to an active ingredient to aid or modify the physical characteristics of the active ingredient (Hazen (2000) *Weed Technology* 14:773-784). As used herein, the adjuvant of this invention improves the stability of the capsule suspension or slurry against coagulation, sedimentation and/or creaming.

In one embodiment, the adjuvant is a polymer. Polymeric adjuvants of use in this invention include nonionic polymers, cationic polymers or anionic polymers. In particular embodiments, the nonionic polymer is a polyvinylpyrrolidone (PVP), polyvinyl alcohol (PVA) polyethylene glycol (PEG), Polyethylene oxide (PEO), polyethylene oxide-polypropylene oxide (PEO-PPO), polyethylene oxide-polypropylene oxide-polyethylene oxide (PEO-PPO-PEO), or a combination thereof. In other embodiments, the cationic polymer is a polydiallyldimethylammonium chloride such as Polyquaterium-6, a vinyl pyrrolidone/dimethylaminoethyl methacrylate copolymer such as Polyquaternium-11, an acrylic acid/methacrylamidopropyl trimethyl ammonium chloride/methyl acrylate terpolymer such as Polyquaternium-47, or a combination thereof. In yet other embodiments, the anionic polymer is a polystyrene sulfonic acid, polyacrylic acid, hyaluronic acid, sodium alginate, sodium carboxymethylcellulose (CMC), or a combination thereof. Such polymeric adjuvants are known in the art and available from commercial sources. See Example 2. In accordance with some embodiments of the invention, the polymeric adjuvant has a molecular weight in the range of 15,000 to 3,000,000. In certain embodiments, the adjuvant has a molecular weight in the range of 50,000 to 1,500,000.

In another embodiment, the adjuvant is a surfactant. In particular embodiments, the surfactant is an anionic surfactant. Anionic surfactants of use in the invention include, e.g., sodium laureth sulfate (SLS), a phosphate ester, or a combination thereof. Exemplary phosphate esters are complex esters of phosphoric acid and ethoxylated cosmetic grade oleyl alcohol and include, e.g., oleth-10-phosphate (a polyoxyethylene (10) oleyl ether phosphate; e.g., CRODAFOS O10A-SS(RB)), and oleth-3-phosphate (a polyoxyethylene (3) oleyl ether phosphate; e.g., CRODAFOS O30A), which are available from commercial sources such as Croda Inc. (Edison, N.J.). See, U.S. Pat. No. 6,117,915. Other phosphate ester surfactants include STEPFAC 8180 and STEPFAC 818, which are available from the Stepan Company; and ETHYLAN PS-121 and ETHYLAN PS-131 phosphate ester surfactant from Akzo Nobel Inc.

Other adjuvants useful in the present invention include polycarbohydrates, such as starch, modified starch, dextrin, maltodextrin, and cellulose derivatives, and their quaternized forms; natural gums such as alginate esters, carrageenan, xanthanes, agar-agar, pectins, pectic acid, and natural gums such as gum arabic, gum tragacanth and gum karaya, guar gums and quaternized guar gums; gelatin, protein hydrolysates and their quaternized forms; synthetic polymers and copolymers, such as poly(vinyl pyrrolidone-co-vinyl acetate), poly(vinyl alcohol-co-vinyl acetate), poly((met)acrylic acid), poly(maleic acid), poly(alkyl(meth)acrylate-co-(meth)acrylic acid), poly(acrylic acid-co-maleic acid) copolymer, poly(alkyleneoxide), poly(vinylmethylether), poly(vinylether-co-maleic anhydride), and the like, as well as poly-(ethyleneimine), poly((meth)acrylamide), poly(alkyleneoxide-co-dimethylsiloxane), poly(amino dimethylsiloxane), and their quarternized forms.

The adjuvant in the formulation of the invention can be used in the range of 0.01% to 5% of the total capsule formulation weight. More preferably, the adjuvant is used in a range of from 0.05 to 0.5% of the total capsule formulation weight.

Active Material. Active materials suitable for use in this invention include without limitation, any combination of fragrance oil, essential oil, plant extract or mixture thereof that is compatible with, and capable of being encapsulated by, a polymer. Individual perfume ingredients that can be included in the capsules of this invention include fragrances containing:

i) hydrocarbons, such as, for example, 3-carene, α-pinene, β-pinene, α-terpinene, γ-terpinene, p-cymene, bisabolene, camphene, caryophyllene, cedrene, farnesene, limonene, longifolene, myrcene, ocimene, valencene, (E,Z)-1,3,5-undecatriene, styrene, and diphenylmethane;

ii) aliphatic alcohols, such as, for example, hexanol, octanol, 3-octanol, 2,6-dimethylheptanol, 2-methyl-2-heptanol, 2-methyl-2-octanol, (E)-2-hexenol, (E)- and (Z)-3-hexenol, 1-octen-3-ol, a mixture of 3,4,5,6,6-pentamethyl-3/4-hepten-2-ol and 3,5,6,6-tetramethyl-4-methyleneheptan-2-ol, (E,Z)-2,6-nonadienol, 3,7-dimethyl-7-methoxyoctan-2-ol, 9-decenol, 10-undecenol, 4-methyl-3-decen-5-ol, aliphatic aldehydes and their acetals such as for example hexanal, heptanal, octanal, nonanal, decanal, undecanal, dodecanal, tridecanal, 2-methyloctanal, 2-methylnonanal, (E)-2-hexenal, (Z)-4-heptenal, 2,6-dimethyl-5-heptenal, 10-undecenal, (E)-4-decenal, 2-dodecenal, 2,6,10-trimethyl-5,9-undecadienal, heptanal-diethylacetal, 1,1-dimethoxy-2,2,5-trimethyl-4-hexene, and citronellyl oxyacetaldehyde;

iii) aliphatic ketones and oximes thereof, such as, for example, 2-heptanone, 2-octanone, 3-octanone, 2-nonanone, 5-methyl-3-heptanone, 5-methyl-3-heptanone oxime, 2,4,4,7-tetramethyl-6-octen-3-one, aliphatic sulfur-containing compounds, such as for example 3-methylthiohexanol, 3-methylthiohexyl acetate, 3-mercaptohexanol, 3-mercaptohexyl acetate, 3-mercaptohexyl butyrate, 3-acetylthiohexyl acetate, 1-menthene-8-thiol, and aliphatic nitriles (e.g., 2-nonenenitrile, 2-tridecenenitrile, 2,12-tridecenenitrile, 3,7-dimethyl-2,6-octadienenitrile, and 3,7-dimethyl-6-octenenitrile);

iv) aliphatic carboxylic acids and esters thereof, such as, for example, (E)- and (Z)-3-hexenylformate, ethyl acetoacetate, isoamyl acetate, hexyl acetate, 3,5,5-trimethylhexyl acetate, 3-methyl-2-butenyl acetate, (E)-2-hexenyl acetate, (E)- and (Z)-3-hexenyl acetate, octyl acetate, 3-octyl acetate, 1-octen-3-yl acetate, ethyl butyrate, butyl butyrate, isoamyl butyrate, hexylbutyrate, (E)- and (Z)-3-hexenyl isobutyrate, hexyl crotonate, ethylisovalerate, ethyl-2-methyl pentanoate, ethyl hexanoate, allyl hexanoate, ethyl heptanoate, allyl heptanoate, ethyl octanoate, ethyl-(E,Z)-2,4-decadienoate, methyl-2-octinate, methyl-2-noninate, allyl-2-isoamyl oxyacetate, and methyl-3,7-dimethyl-2,6-octadienoate;

v) acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as formates, acetates, propionates, isobutyrates, butyrates, isovalerates, pentanoates, hexanoates, crotonates, tiglinates and 3-methyl-2-butenoates thereof;

vi) acyclic terpene aldehydes and ketones, such as, for example, geranial, neral, citronellal, 7-hydroxy-3,7-dimethyloctanal, 7-methoxy-3,7-dimethyloctanal, 2,6,10-trimethyl-9-undecenal, α-sinensal, β-sinensal, geranylacetone, as well as the dimethyl- and diethylacetals of geranial, neral and 7-hydroxy-3,7-dimethyloctanal;

vii) cyclic terpene alcohols, such as, for example, menthol, isopulegol, alpha-terpineol, terpinen-4-ol, menthan-8-ol, menthan-1-ol, menthan-7-ol, borneol, isoborneol, linalool oxide, nopol, cedrol, ambrinol, vetiverol, guaiol, and the formates, acetates, propionates, isobutyrates, butyrates, isovalerates, pentanoates, hexanoates, crotonates, tiglinates and 3-methyl-2-butenoates of alpha-terpineol, terpinen-4-ol, methan-8-ol, methan-1-ol, methan-7-ol, borneol, isoborneol, linalool oxide, nopol, cedrol, ambrinol, vetiverol, and guaiol;

viii) cyclic terpene aldehydes and ketones, such as, for example, menthone, isomenthone, 8-mercaptomenthan-3-one, carvone, camphor, fenchone, α-ionone, β-ionone, α-n-methylionone, β-n-methylionone, α-isomethylionone, β-isomethylionone, alpha-irone, α-damascone, β-damascone, β-damascenone, δ-damascone, γ-damascone, 1-(2,4,4-trimethyl-2-cyclohexen-1-yl)-2-buten-1-one, 1,3,4,6,7,8a-hexahydro-1,1,5,5-tetramethyl-2H-2,4-a-methanonaphthalen-8(5H-)-one, nootkatone, dihydronootkatone; acetylated cedarwood oil (cedryl methyl ketone);

ix) cyclic alcohols, such as, for example, 4-tert-butylcyclohexanol, 3,3,5-trimethylcyclohexanol, 3-isocamphylcyclohexanol, 2,6,9-trimethyl-Z2,Z5,E9-cyclododecatrien-1-ol, 2-isobutyl-4-methyltetrahydro-2H-pyran-4-ol;

x) cycloaliphatic alcohols, such as, for example, alpha,3,3-trimethylcyclo-hexylmethanol, 2-methyl-4-(2,2,3-trimethyl-3-cyclopent-1-yl)butanol, 2-methyl-4-(2,2,3-trimethyl-3-cyclopent-1-yl)-2-buten-1-ol, 2-ethyl-4-(2,2,3-trimethyl-3-cyclopent-1-yl)-2-buten-1-ol, 3-methyl-5-(2,2,3-trimethyl-3-cyclopent-1-yl)-pentan-2-ol, 3-methyl-5-(2,2,3-trimethyl-3-cyclopent-1-yl)-4-penten-2-ol, 3,3-dimethyl-5-(2,2,3-trimethyl-3-cyclopent-1-yl)-4-penten-2-ol, 1-(2,2,6-trimethylcyclohexyl)pentan-3-ol, 1-(2,2,6-trimethylcyclohexyl)hexan-3-ol;

xi) cyclic and cycloaliphatic ethers, such as, for example, cineole, cedryl methyl ether, cyclododecyl methyl ether;

xii) (ethoxymethoxy)cyclododecane; alpha-cedrene epoxide, 3a,6,6,9a-tetramethyldodecahydronaphtho[2,1-b]furan, 3a-ethyl-6,6,9a-trimethyldodecahydronaphtho[2,1-b]furan, 1,5,9-trimethyl-13-oxabicyclo[10.1.0]-trideca-4,8-diene, rose oxide, 2-(2,4-dimethyl-3-cyclohexen-1-yl)-5-methyl-5-(1-methylpropyl)-1,3-dioxan-;

xiii) cyclic ketones, such as, for example, 4-tert-butylcyclohexanone, 2,2,5-trimethyl-5-pentylcyclopentanone, 2-heptylcyclopentanone, 2-pentylcyclopentanone, 2-hydroxy-3-methyl-2-cyclopenten-1-one, 3-methyl-cis-2-penten-1-yl-2-cyclopenten-1-one, 3-methyl-2-pentyl-2-cyclopenten-1-one, 3-methyl-4-cyclopentadecenone, 3-methyl-5-cyclopentadecenone, 3-methylcyclopentadecanone, 4-(1-ethoxyvinyl)-3,3,5,5-tetramethylcyclohexanone, 4-tert-pentylcyclohexanone, 5-cyclohexadecen-1-one, 6,7-dihydro-1,1,2,3,3-pentamethyl-4(5H)-indanone, 5-cyclohexadecen-1-one, 8-cyclohexadecen-1-one, 9-cycloheptadecen-1-one, cyclopentadecanone, cycloaliphatic aldehydes, such as, for example, 2,4-dimethyl-3-cyclohexene carbaldehyde, 2-methyl-4-(2,2,6-trimethyl-cyclohexen-1-yl)-2-butenal, 4-(4-hydroxy-4-methylpentyl)-3-cyclohexene carbaldehyde, 4-(4-methyl-3-penten-1-yl)-3-cyclohexene carbaldehyde;

xiv) cycloaliphatic ketones, such as, for example, 1-(3,3-dimethylcyclohexyl)-4-penten-1-one, 1-(5,5-dimethyl-1-cyclohexen-1-yl)-4-penten-1-one, 2,3,8,8-tetramethyl-1,2,3,4,5,6,7,8-octahydro-2-naphtalenyl methyl-ketone, methyl-2,6,10-trimethyl-2,5,9-cyclododecatrienyl ketone, tert-butyl-(2,4-dimethyl-3-cyclohexen-1-yl)ketone;

xv) esters of cyclic alcohols, such as, for example, 2-tert-butylcyclohexyl acetate, 4-tert-butylcyclohexyl acetate, 2-tert-pentylcyclohexyl acetate, 4-tert-pentylcyclohexyl acetate, decahydro-2-naphthyl acetate, 3-pentyltetrahydro-2H-pyran-4-yl acetate, decahydro-2,5,5,8a-tetramethyl-2-naphthyl acetate, 4,7-methano-3a,4,5,6,7,7a-hexahydro-5 or 6-indenyl acetate, 4,7-methano-3a,4,5,6,7,7a-hexahydro-5 or 6-indenyl propionate, 4,7-methano-3a,4,5,6,7,7a-hexahydro-5 or 6-indenyl-isobutyrate, 4,7-methanooctahydro-5 or 6-indenyl acetate;

xvi) esters of cycloaliphatic carboxylic acids, such as, for example, allyl 3-cyclohexyl-propionate, allyl cyclohexyl oxyacetate, methyl dihydrojasmonate, methyl jasmonate, methyl 2-hexyl-3-oxocyclopentanecarboxylate, ethyl 2-ethyl-6,6-dimethyl-2-cyclohexenecarboxylate, ethyl 2,3,6,6-tetramethyl-2-cyclohexenecarboxylate, ethyl 2-methyl-1,3-dioxolane-2-acetate;

xvii) aromatic and aliphatic alcohols, such as, for example, benzyl alcohol, 1-phenylethyl alcohol, 2-phenylethyl alcohol, 3-phenylpropanol, 2-phenylpropanol, 2-phenoxyethanol, 2,2-dimethyl-3-phenylpropanol, 2,2-dimethyl-3-(3-methylphenyl)propanol, 1,1-dimethyl-2-phenylethyl alcohol, 1,1-dimethyl-3-phenylpropanol, 1-ethyl-1-methyl-3-phenylpropanol, 2-methyl-5-phenylpentanol, 3-methyl-5-phenylpentanol, 3-phenyl-2-propen-1-ol, 4-methoxybenzyl alcohol, 1-(4-isopropylphenyl)ethanol;

xviii) esters of aliphatic alcohols and aliphatic carboxylic acids, such as, for example, benzyl acetate, benzyl propionate, benzyl isobutyrate, benzyl isovalerate, 2-phenylethyl acetate, 2-phenylethyl propionate, 2-phenylethyl isobutyrate, 2-phenylethyl isovalerate, 1-phenylethyl acetate, α-trichloromethylbenzyl acetate, α,α-dimethylphenylethyl acetate, alpha, alpha-dimethylphenylethyl butyrate, cinnamyl acetate, 2-phenoxyethyl isobutyrate, 4-methoxybenzyl acetate, araliphatic ethers, such as for example 2-phenylethyl methyl ether, 2-phenylethyl isoamyl ether, 2-phenylethyl-1-ethoxyethyl ether, phenylacetaldehyde dimethyl acetal, phenylacetaldehyde diethyl acetal, hydratropaaldehyde dimethyl acetal, phenylacetaldehyde glycerol acetal, 2,4,6-trimethyl-4-phenyl-1,3-dioxane, 4,4a,5,9b-tetrahydroindeno[1,2-d]-m-dioxin, 4,4a,5,9b-tetrahydro-2,4-dimethylindeno[1,2-d]-m-dioxin;

xix) aromatic and aliphatic aldehydes, such as, for example, benzaldehyde; phenylacetaldehyde, 3-phenylpropanal, hydratropaldehyde, 4-methylbenzaldehyde, 4-methylphenylacetaldehyde, 3-(4-ethylphenyl)-2,2-dimethylpropanal, 2-methyl-3-(4-isopropylphenyl)propanal, 2-methyl-3-(4-tert-butylphenyl)propanal, 3-(4-tert-butylphenyl) propanal, cinnamaldehyde, alpha-butylcinnamaldehyde, alpha-amylcinnamaldehyde, alpha-hexylcinnamaldehyde, 3-methyl-5-phenylpentanal, 4-methoxybenzaldehyde, 4-hydroxy-3-methoxybenzaldehyde, 4-hydroxy-3-ethoxybenzaldehyde, 3,4-methylene-dioxybenzaldehyde, 3,4-dimethoxybenzaldehyde, 2-methyl-3-(4-methoxyphenyl)propanal, 2-methyl-3-(4-methylendioxyphenyl)propanal;

xx) aromatic and aliphatic ketones, such as, for example, acetophenone, 4-methylacetophenone, 4-methoxyacetophenone, 4-tert-butyl-2,6-dimethylacetophenone, 4-phenyl-2-butanone, 4-(4-hydroxyphenyl)-2-butanone, 1-(2-naphthalenyl)ethanone, benzophenone, 1,1,2,3,3,6-hexamethyl-5-indanyl methyl ketone, 6-tert-butyl-1,1-dimethyl-4-indanyl methyl ketone, 1-[2,3-dihydro-1,1,2,6-tetramethyl-3-(1-methyl-ethyl)-1H-5-indenyl]ethanone, 5',6',7',8'-tetrahydro-3',5',5',6',8',8'-hexamethyl-2-acetonaphthone;

xxi) aromatic and araliphatic carboxylic acids and esters thereof, such as, for example, benzoic acid, phenylacetic acid, methyl benzoate, ethyl benzoate, hexyl benzoate, benzyl benzoate, methyl phenylacetate, ethyl phenylacetate, geranyl phenylacetate, phenylethyl phenylacetate, methyl cinnamate, ethyl cinnamate, benzyl cinnamate, phenylethyl cinnamate, cinnamyl cinnamate, allyl phenoxyacetate, methyl salicylate, isoamyl salicylate, hexyl salicylate, cyclohexyl salicylate, cis-3-hexenyl salicylate, benzyl salicylate, phenylethyl salicylate, methyl 2,4-dihydroxy-3,6-dimethylbenzoate, ethyl 3-phenylglycidate, ethyl 3-methyl-3-phenylglycidate;

xxii) nitrogen-containing aromatic compounds, such as, for example, 2,4,6-trinitro-1,3-dimethyl-5-tert-butylbenzene, 3,5-dinitro-2,6-dimethyl-4-tert-butylacetophenone, cinnamonitrile, 5-phenyl-3-methyl-2-pentenonitrile, 5-phenyl-3-methylpentanonitrile, methyl anthranilate, methyl-N-methylanthranilate, Schiff's bases of methyl anthranilate with 7-hydroxy-3,7-dimethyloctanal, 2-methyl-3-(4-tert-butylphenyl)propanal or 2,4-dimethyl-3-cyclohexene carbaldehyde, 6-isopropylquinoline, 6-isobutylquinoline, 6-sec-butylquinoline, indole, skatole, 2-methoxy-3-isopropylpyrazine, 2-isobutyl-3-methoxypyrazine;

xxiii) phenols, phenyl ethers and phenyl esters, such as, for example, estragole, anethole, eugenol, eugenyl methyl ether, isoeugenol, isoeugenol methyl ether, thymol, carvacrol, diphenyl ether, beta-naphthyl methyl ether, beta-naphthyl ethyl ether, beta-naphthyl isobutyl ether, 1,4-dimethoxybenzene, eugenyl acetate, 2-methoxy-4-methylphenol, 2-ethoxy-5-(1-propenyl)phenol, p-cresyl phenylacetate;

xxiv) heterocyclic compounds, such as, for example, 2,5-dimethyl-4-hydroxy-2H-furan-3-one, 2-ethyl-4-hydroxy-5-methyl-2H-furan-3-one, 3-hydroxy-2-methyl-4H-pyran-4-one, 2-ethyl-3-hydroxy-4H-pyran-4-one;

xxv) lactones, such as, for example, 1,4-octanolide, 3-methyl-1,4-octanolide, 1,4-nonanolide, 1,4-decanolide, 8-decen-1,4-olide, 1,4-undecanolide, 1,4-dodecanolide, 1,5-decanolide, 1,5-dodecanolide, 1,15-pentadecanolide, cis- and trans-11-pentadecen-1,15-olide, cis- and trans-12-pentadecen-1,15-olide, 1,16-hexadecanolide, 9-hexadecen-1,16-olide, 10-oxa-1,16-hexadecanolide, 11-oxa-1,16-hexadecanolide, 12-oxa-1,16-hexadecanolide, ethylene-1,12-dodecanedioate, ethylene-1,13-tridecanedioate, coumarin, 2,3-dihydrocoumarin, and octahydrocoumarin; and xxvi) essential oils, concretes, absolutes, resins, resinoids, balsams, tinctures such as for example ambergris tincture, amyris oil, angelica seed oil, angelica root oil, aniseed oil, valerian oil, basil oil, tree moss absolute, bay oil, armoise oil, benzoe resinoid, bergamot oil, beeswax absolute, birch tar oil, bitter almond oil, savory oil, buchu leaf oil, cabreuva oil, cade oil, calamus oil, camphor oil, cananga oil, cardamom oil, cascarilla oil, cassia oil, cassie absolute, castoreum absolute, cedar leaf oil, cedar wood oil, cistus oil, citronella oil, lemon oil, copaiba balsam, copaiba balsam oil, coriander oil, costus root oil, cumin oil, cypress oil, davana oil, dill weed oil, dill seed oil, eau de brouts absolute, oakmoss absolute, elemi oil, estragon oil, eucalyptus citriodora oil, eucalyptus oil (cineole type), fennel oil, fir needle oil, galbanum oil, galbanum resin, geranium oil, grapefruit oil, guaiacwood oil, gurjun balsam, gurjun balsam oil, helichrysum absolute, helichrysum oil, ginger oil, iris root absolute, iris root oil, jasmine absolute, calamus oil, blue camomile oil, Roman camomile oil, carrot seed oil, cascarilla oil, pine needle oil, spearmint oil, caraway oil, labdanum oil, labdanum absolute, labdanum resin, lavandin absolute, lavandin oil, lavender absolute, lavender oil, lemon-grass oil, lovage oil, lime oil distilled, lime oil expressed, linaloe oil, *Litsea cubeba* oil, laurel leaf oil, mace oil, marjoram oil, mandarin oil, massoi (bark) oil, mimosa absolute, ambrette seed oil, musk tincture, clary sage oil, nutmeg oil, myrrh absolute, myrrh oil, myrtle oil, clove leaf oil, clove bud oil, neroli oil, olibanum absolute, olibanum oil, opopanax oil, orange flower absolute, orange oil, origanum oil, palmarosa oil, patchouli oil, perilla oil, Peru balsam oil, parsley leaf oil, parsley seed oil, petitgrain oil, peppermint oil, pepper oil, pimento oil, pine oil, pennyroyal oil, rose absolute, rosewood oil, rose oil, rosemary oil, Dalmatian sage oil, Spanish sage oil, sandal-wood oil, celery seed oil: spike-lavender oil, star anise oil, storax oil, tagetes oil, fir needle oil, tea tree oil, turpentine oil, thyme oil, Tolu balsam, tonka bean absolute, tuberose absolute, vanilla extract, violet leaf absolute, verbena oil, vetiver oil, juniperberry oil, wine lees oil, wormwood oil, wintergreen oil, ylang-ylang oil, hyssop oil, civet absolute, cinnamon leaf oil, cinnamon bark oil, and fractions thereof or ingredients isolated therefrom.

In some embodiments, the amount of encapsulated fragrance oil is from about 80% to about 5% of the total core-shell capsule suspension or capsule slurry, preferably from about 60% to about 10% of the total capsule suspension or capsule slurry, and most preferably from about 50% to about 20% of the total capsule suspension or capsule slurry.

In some embodiments, the amount of encapsulated fragrance oil is from about 5% to about 60% of the total weight of the silica capsule formulation, preferably from about 10% to about 50% of the total weight of the silica capsule formulation.

In addition to the fragrance materials, the present invention also contemplates the incorporation of other core additives including solvent, emollients, particles, polymeric core modifiers and/or core modifier materials encapsulated by the encapsulating polymer.

Solvent materials are hydrophobic materials that are miscible in the fragrance materials used in the present invention. Suitable solvents are those having reasonable affinity for the fragrance chemicals and a Clog P greater than 3.3, preferably greater than 6 and most preferably greater than 10. Suitable materials include, but are not limited to triglyceride oil, mono and diglycerides, mineral oil, silicone oil, diethyl phthalate, polyalpha olefins, castor oil and isopropyl myristate. In a highly preferred embodiment the solvent materials are combined with fragrance materials that have high Clog P values as set forth above. It should be noted that selecting a solvent and fragrance with high affinity for each other will result in the most pronounced improvement in stability. This specific affinity may be measured by determining the Solvent-Water partition coefficient for the fragrance material. Appropriate solvents include, but are not limited to, mono-, di- and tri-esters, and mixtures thereof, of fatty acids and glycerin. The fatty acid chain can range from C4-C26. Also, the fatty acid chain can have any level of unsaturation. For instance capric/caprylic triglyceride known as NEOBEE M5 (Stepan Corporation). Other suitable examples are the CAPMUL series by Abitec Corporation, for instance CAPMUL MCM. Isopropyl myristate fatty acid esters of polyglycerol oligomers include $R_2CO$—$[OCH_2$—$CH(OCOR_1)$—$CH_2O$—$]_n$, where $R_1$ and $R_2$ can be H or C4-26 aliphatic chains, or mixtures thereof, and n ranges between 2-50, preferably 2-30. Nonionic fatty alcohol alkoxylates like the NEODOL surfactants by BASF, the DOBANOL surfactants by Shell Corporation or the BIO-SOFT surfactants by Stepan, wherein the alkoxy group is ethoxy, propoxy, butoxy, or mixtures thereof. In addition, these surfactants can be end-capped with methyl groups in order to increase their hydrophobicity. Di- and tri-fatty acid chain containing nonionic, anionic and cationic surfactants, and mixtures thereof are also contemplated, as are fatty acid esters of polyethylene glycol, polypropylene glycol, and polybutylene glycol, or mixtures thereof. Polyalphaolefins such as the EXXONMOBIL PURESYM PAO line; esters such as the EXXONMOBIL PURESYN esters; mineral oil; silicone oils such polydimethyl siloxane and polydimethylcyclosiloxane; diethyl phthalate; and di-isodecyl adipate can also be included. In certain embodiments, ester oils have at least one ester group in the molecule. One type of common ester oil useful in the present invention are the fatty acid mono and polyesters such as cetyl octanoate, octyl isononanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester and polyesters, sorbitol ester, and the like. A second type of useful ester oil is predominantly composed of triglycerides and modified triglycerides. These include vegetable oils such as jojoba, soybean, canola, sunflower, safflower, rice bran, avocado, almond, olive, sesame, persic, castor, coconut, and mink oils. Synthetic triglycerides can also be employed provided they are liquid at room temperature. Modified triglycerides include materials such as ethoxylated and maleated triglyceride derivatives provided they are liquids. Proprietary ester blends such as those sold by FINETEX as FINSOLV are also suitable, as is ethylhexanoic acid glyceride. A third type of ester oil is liquid polyester formed from the reaction of a dicarboxylic acid and a diol. Examples of polyesters suitable for the present invention are the polyesters marketed by EXXONMOBIL under the trade name PURESYN ESTER.

Nanoscale solid particulate materials such as those disclosed in U.S. Pat. No. 7,833,960 may also be incorporated into the core and may be selected from, but not limited to, metal or metallic particles, metal alloys, polymer particles, wax particles, inorganic particulates, minerals and clay particles.

The metal particles can be selected from a non-limiting list of main group elements, transition metal and post-transition metal elements including aluminum (Al), silica (Si), Titanium (Ti), chromium (Cr), manganese (Mn), iron (Fe), nickel (Ni), cobalt (Co), copper (Cu), gold (Au), silver (Ag), platinum (Pt) and palladium (Pd).

Polymer particles of any chemical composition and nature are suitable for the present invention as long as their physical dimension falls into the prescribed region and a liquid core is generated. The polymer particles can be selected from a nonlimiting list of polymers and co-copolymer based on polystyrene, polyvinyl acetate, polylactides, polyglycolides, ethylene maleic anhydride copolymer, polyethylene, polypropylene, polyamide, polyimide, polycarbonate, polyester, polyurethane, polyurea, cellulose and cellulose, and combinations and mixture of such polymers.

The inorganic particulate can be selected from a non-limiting list including silica, titanium dioxide ($TiO_2$), zinc oxide (ZnO), $Fe_2O_3$, and other metal oxides such as but not limited to NiO, $Al_2O_3$, SnO, $SnO_2$, $CeO_2$, ZnO, CdO, $RuO_2$, FeO, CuO, AgO, $MnO_2$, as well as other transition metal oxides.

Examples of nanoscaled materials include AEROSIL R812, which has a particle size of less than 25 nm according to the specification from the manufacture, Degussa Corp. Other suitable materials from Degussa include, but not limited to, AEROSIL R972, AEROSIL R974, AEROSIL R104, AEROSIL R106, AEROSIL R202, AEROSIL R805, AEROSIL R812, AEROSIL R812S, AEROSIL R816, AEROSIL R7200, AEROSIL R9200, and AEROXIDE $TiO_2$ P25, AEROXIDE T805, AEROXIDE LE1, AEROXIDE LE2, AEROXIDE $TiO_2$ NKT 90, AEROXIDE Alu C805, titanium dioxide PF2, SIPERNAT D110, SIPERNAT D-380. The hydrophobic materials from Deguassa Corp. such as including AEROSILE R812 and R972 are especially preferred.

Nanoscaled materials such as UVINUL $TiO_2$ and Z-COTE HP1 manufactured by BASF can also be used as well as and TI-PURE titanium dioxide, TI-PURE R-700, and TI-SELECT. Additional suitable materials include TS-6200 from Dupont and ZEROFREE 516, HUBERDERM 2000 and HUBERDERM 1000 from the J. M. Huber Corporation, Havre De Grace, Md. Silica products such as SYLOID 63, 244, 72, 63FP 244FP, 72FP, SYLOX 15, 2 and Zeolites such as SYLOSIV A3, SYLOSIV A4 and SYLOSIV K300 from Grace Davison can also be used.

Polymeric core modifiers are also contemplated. It has been found that the addition of hydrophobic polymers to the core can also improve stability by slowing diffusion of the fragrance from the core. The level of polymer is normally less than 80% of the core by weight, preferably less than 50%, and most preferably less than 20%. The basic requirement for the polymer is that it be miscible or compatible with the other components of the core, namely the fragrance and other solvent. Preferably, the polymer also thickens or gels the core, thus further reducing diffusion. Polymeric core modifiers include copolymers of ethylene; copolymers of ethylene and vinyl acetate (ELVAX polymers by DOW Corporation); copolymers of ethylene and vinyl alcohol (EVAL polymers by Kuraray); ethylene/acrylic elastomers such as VALNAC polymers by Dupont; polyvinyl polymers, such as polyvinyl acetate; alkyl-substituted cellulose, such as ethyl cellulose (ETHOCEL made by DOW Corporation) and hydroxypropyl celluloses (KLUCEL polymers by Hercules); cellulose acetate butyrate available from Eastman Chemical; polyacrylates (e.g., AMPHOMER, DEMACRYL LT and DERMACRYL 79, made by National Starch and Chemical Company, the AMERHOLD polymers by Amerchol Corporation, and ACUDYNE 258 by ISP Corporation); copolymers of acrylic or methacrylic acid and fatty esters of acrylic or methacrylic acid such as INTELIMER POLYMERS made by Landec Corporation (see also U.S. Pat. Nos. 4,830,855, 5,665,822, 5,783,302, 6,255,367 and 6,492,462); polypropylene oxide; polybutylene oxide of poly(tetrahydrofuran); polyethylene terephthalate; polyurethanes (DYNAM X by National Starch); alkyl esters of poly(methyl vinyl ether); maleic anhydride copolymers, such as the GANTREZ copolymers and OMNIREZ 2000 by ISP Corporation; carboxylic acid esters of polyamines, e.g., ester-terminated polyamides (ETPA) made by Arizona Chemical Company; polyvinyl pyrrolidone (LUVISKOL series of BASF); block copolymers of ethylene oxide, propylene oxide and/or butylenes oxide including, e.g., PLURONIC and SYNPERONIC polymers/dispersants by BASF. Another class of polymers include polyethylene oxide-co-propyleneoxide-co-butylene oxide polymers of any ethylene oxide/propylene oxide/butylene oxide ratio with cationic groups resulting in a net theoretical positive charge or equal to zero (amphoteric). The general structure is:

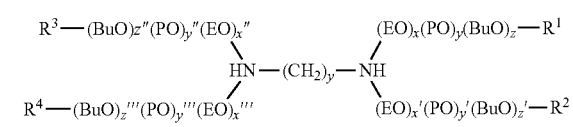

where $R^1$, $R^2$, $R^3$, and $R^4$ are independently H or any alkyl or fatty alkyl chain group. Examples of such polymers are the commercially known as TETRONICS by BASF Corporation.

Sacrificial core ingredients can also be included. These ingredients are designed to be lost during or after manufacture and include, but are not limited to, highly water soluble or volatile materials.

The level of solvent materials, particles or polymeric core modifiers in the core encapsulated by the encapsulating polymer should be greater than about 10 weight percent, preferably greater than about 30 weight percent and most preferably greater than about 70 weight percent. In addition to the solvent, it is preferred that higher Clog P fragrance materials are employed. It is preferred that greater than about 60 weight percent, preferably greater than 80 and more preferably greater than about 90 weight percent of the fragrance chemicals have Clog P values of greater than about 3.3, preferably greater than about 4 and most preferably greater than about 4.5. Those with skill in the art will appreciate that many formulations can be created employing various solvents and fragrance chemicals. The use of a high level of high Clog P fragrance chemicals will likely require a lower level of hydrophobic solvent than fragrance chemicals with lower Clog P to achieve similar performance stability. As those with skill in the art will appreciate, in a highly preferred embodiment, high Clog P fragrance chemicals and hydrophobic solvents comprise greater than about 80, preferably more than about 90 and most preferably greater than 95 weight percent of the fragrance composition. As discussed above, specific Clog P values may be measured between candidate solvents and water for the fragrance materials to be included in the core. In this way, an optimum solvent choice may be made. In fact, since most fragrances will have many ingredients, it may be preferable to measure the partitioning of a specific fragrance blend in solvent and water in order to determine the effect of any material interactions.

Other active materials that can be included the in capsules of this invention include antimicrobial agents such as thymol, 2-hydroxy-4,2,4-trichlorodiphenylether, triclocarban; organic sunscreen actives such as oxybenzone, octylmethoxy cinnamate, butylmethoxy dibenzoyln ethane, p-aminobenzoic acid and octyl dimethyl-p-aminobenzoic acid; vitamins such as Vitamin A, Vitamin C and Vitamin E or esters thereof; and malodor counteracting ingredients including, but not limited to, an α,β-unsaturated carbonyl compounds including but not limited to those disclosed in U.S. Pat. No. 6,610,648 and EP 2,524,704, amyl cinnamaldehyde, benzophenone, benzyl benzoate, benzyl isoeugenol, benzyl phenyl acetate, benzyl salicylate, butyl cinnamate, cinnamyl butyrate, cinnamyl isovalerate, cinnamyl propionate, decyl acetate, ethyl myristate, isobutyl cinnamate, isoamyl salicylate, phenethyl benzoate, phenethyl phenyl acetate, triethyl citrate, tripropylene glycol n-butyl ether, isomers of bicyclo[2.2.1]hept-5-ene-2-carboxylic acid, ethyl ester, and zinc undecenylate.

As used herein olfactory effective amount is understood to mean the amount of compound in perfume compositions the individual component will contribute to its particular olfactory characteristics, but the olfactory effect of the fragrance composition will be the sum of the effects of each of the fragrance ingredients. Thus, the fragrances of the invention can be used to alter the aroma characteristics of the perfume composition by modifying the olfactory reaction contributed by another ingredient in the composition. The amount will vary depending on many factors including other ingredients, their relative amounts and the effect that is desired.

Emulsions of the active materials can be prepared using any conventional technique such as mechanical means (e.g., homogenization with a high shear mixer), ultrasound or sonication and in some embodiments, the emulsions are diluted. Moreover, any conventional sol-gel process can be employed for preparing the microcapsule particles of the invention. For example, emulsions of the invention can be mixed under constant mixing and then allowed to cure at room temperature (i.e., 20° C. to 25° C.) until sol-gel capsules have formed. In other embodiments, emulsions of the invention are mixed under constant mixing and the mixture is allowed to cure at high temperature until sol-gel capsules have formed. For the purposes of the present invention, "high temperature" is intended to mean a temperature in the range of 30° C. to 70° C., or more particularly 40° C. to 60° C. In particular embodiments, the sol-gel mixture is cured at 50° C. In some embodiments, the method can further include the use of an emulsifier, which is combined with one or more emulsions prior to homogenization.

The diameter of the capsules produced in accordance with this invention can vary from about 10 nanometers to about 1000 microns, preferably from about 50 nanometers to about 100 microns and is most preferably from about 2 to about 15 microns. The capsule distribution can be narrow, broad, or multi-modal. Multi-modal distributions may be composed of different types of capsule chemistries.

Applications. The present invention is well-suited for use in personal care products including, without limitation, deodorants and antiperspirants, shampoos, hair conditioners, hair rinses, hair refreshers, body washes, soaps products, as well as beauty care products such as fine fragrance, Eau De Toilette products, and the like. In particular embodiments, the formulation of the invention is of use in an aerosol antiperspirant, stick antiperspirant, roll-on antiperspirant, emulsion spray antiperspirant, clear emulsion stick antiperspirant, soft solid antiperspirant, emulsion roll-on antiperspirant, clear emulsion stick antiperspirant, opaque emulsion stick antiperspirant, clear gel antiperspirant, clear stick deodorant or spray deodorant. Exemplary personal care product formulations are provided in Examples 6-12.

The present invention is also well-suited for use in fabric care products such as rinse conditioners and liquid and powder detergents; home care products such as all-purpose cleaners and fabric refreshers; personal hygiene products such as hand sanitizers; and oral care products such as tooth powder, all of which are known in the art. For example, liquid dish detergents are described in U.S. Pat. Nos. 6,069, 122 and 5,990,065; automatic dish detergent products are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562. Liquid laundry detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Shampoo and conditioners that can employ the present invention include U.S. Pat. Nos. 6,162,423, 5,968,286, 5,935561, 5,932,203, 5,837,661, 5,776,443, 5,756,436, 5,661,118, 5,618,523, 5,275,755, 5,085,857, 4,673,568, 4,387,090 and 4,705,681.

The invention is described in greater detail by the following non-limiting examples.

EXAMPLE 1

Preparation of Silica Capsules with a Sol-Gel Precursor

This example illustrates the preparation of silica capsules using a precursor where the central silicon atom is coordinated to four alkoxy groups. The empirical formula is $Si(OR)_4$, where —OR is an alkoxy group and is hydrolyzable upon dispersion in water. In general, the method involves preparing a concentrated fragrance emulsification, diluting the fragrance emulsion to the desired concentration, and adding TEOS.

Preparation of Concentrated Fragrance Emulsion. Two hundred and six grams fragrance oil core (80% fragrance with 20% NEOBEE M5) was weighed out and placed in round bottom vessel. In a separate vessel, a 1.0% aqueous surfactant solution (120 g) was prepared by dissolving the needed amount of 30% cetyltrimethylammonium chloride (CTAC) surfactant solution in distilled water. The oil phase was then poured into the aqueous phase and the mixture was homogenized with a high shear mixer (Ultra Turrax T 25 Basic, IKA, Werke). Four drops of defoamer was added to suppress the foaming generated Preparation of Diluted Fragrance Emulsion. Diluted fragrance emulsion was prepared by blending the concentrated fragrance emulsion with the desired amount of water to generate the desired concentration.

Preparation of Silica Capsules. The formation of silica capsules was achieved by adding a single precursor to the diluted fragrance emulsion. The amount of precursor added was routinely determined by the wall polymer level needed and was generally 1% to 30% of the final formulation. Typically, the desired amount of precursor, tetraethyl orthosilicate (TEOS) was weighted out (35.91 g in this example) and placed in a clean and dry dropping funnel. The TEOS was then added dropwise into the diluted fragrance emulsion under constant mixing. The mixing speed was reduced once the addition of TEOS was complete. The system was then left at room and cured for an extended period of time. The pH of the system was maintained at approximately 3 to 4. The capsule formed was well dispersed and generally had a particle size ranging from submicron to one hundred micron depending on the emulsifier and shear rates used.

The physical properties of the fragrance ingredients and the slurries prepared therewith are listed in Table 1.

TABLE 1

| Sample | Fragrance | Fragrance Concentration | Density (g/mL) |
|---|---|---|---|
| 1 | Posh Special Neat Oil | 100% | 0.9625 |
| 2 | Fresh Extreme Neat Oil | 100% | 0.9624 |
| 3 | NEOBEE Neat Oil | 100% | 0.9466 |
| 4 | Posh Special Silica Slurry | 31% in slurry | 0.9818 |
| 5 | Fresh Extreme Silica Slurry | 31% in slurry | 0.992 |

The storage stability of Samples 4 and 5 was analyzed. Sample 4 exhibited partial capsule separation from the aqueous phase in four weeks with gelling on the top. Sample 5 exhibited complete separation of capsule from the aqueous phase in four weeks with gelling on the top.

EXAMPLE 2

Preparation of Silica Capsule Slurry with Improved Stability

To improve stability, thirty grams of the capsule slurry as prepared in Example 1 was weighed out and 0.15 g of CRODAFOS 010A-SS-(RB) surfactant (oleth-10-phosphate, a complex ester of phosphoric acid and ethoxylated cosmetic grade oleyl alcohol; Croda, Edison, N.J.) was added after the CRODAFOS 010A-SS-(RB) was gently heated to its liquid state. The mixture was stirred for approximately 30 minutes via an overhead IKA lab mixer until the surfactant was completely dissolved and homogeneous.

Alternatively, a 10% solution of CRODAFOS 010A-SS-(RB) emulsifier was prepared by dissolving 10 grams of the material in 90 grams under heating. The stabilized capsule slurry was prepared by mixing 570 grams of the fragrance capsule slurry prepared as in Example 1 with 30 grams of the 10% solution of CRODAFOS 010A-SS-(RB) emulsifier under consistent mixing for 30 minutes.

Evaluation of Capsule Stability by Microscopy. The stability of the capsules was evaluated by diluting the slurry with water. The diluted sample was placed on microscopic slides and monitored overnight. Microscopic analysis indicated that well-formed silica capsules were prepared as fresh sample in water. Some breakage of the capsules was seen after the capsules were dried overnight on a microscopy slide. However, in general, the capsules retained their structural integrity after drying for 3 days in a microscopy slide.

Evaluation of Capsule Slurry Stability. The slurry stability was evaluated by aging the samples with and without the CRODAFOS 010A-SS-(RB) surfactant over a period of 4 weeks. Photographic pictures were taken to illustrate the stability of the samples. The results of this analysis indicated that there was no separation seen for the capsule slurry prepared with the CRODAFOS 010A-SS-(RB) surfactant, while samples prepared without CRODAFOS 010A-SS-(RB) surfactant displayed significant separation, demonstrating the benefit of the phosphate ester.

EXAMPLE 3

Preparation of Silica Capsules Incorporating Surfactants and Polymers as Adjuvants To evaluate other adjuvants, silica capsule slurries were prepared as described in Example 1 and combined with one or more adjuvants as listed in Table 2. A general procedure for preparing the formulations is provided using Polyquaternium-6 as an example. A 5% Polyquaternium-6 solution was prepared by adding water to a 40% Polyquaternium-6 solution available commercially from Nalco. The diluted polymer solution was then mixed with the slice capsule slurry to give silica capsules with the appropriate level of adjuvant. The mixture was homogenized using an overhead misted at 500 rpm for 25 minutes before being placed in oven for storage tests.

TABLE 2

| Sample | Adjuvant | Components of Adjuvant | Conc. Used |
|---|---|---|---|
| 1 | LUVIQUAT PQ11 Polyquaternium-11 | Vinyl pyrrolidone/dimethylaminoethyl methacrylate copolymer, cationic polymer | 0.5% |
| 2 | MERQUAT 100 Polyquaternium-6 | Poly(diallyldimethyl ammonium chloride), cationic polymer | 0.45% |
| 3 | MERQUAT 2001 Polyquaternium-47 | Acrylic acid/methacrylamidopropyl trimethyl ammonium chloride/methyl acrylate terpolymer, cationic polymer | 0.04% |
| 4 | LUVISKOL K90W | Polyvinylpyrrolidone, non-ionic polymer | 0.2% |
| 5 | LUVISKOL K30 | Polyvinylpyrrolidone, non-ionic polymer | 0.2% |
| 6 | LUVISKOL K17 | Polyvinylpyrrolidone, non-ionic polymer | 0.4% |
| 7 | LUVISKOL VA 73W | Vinylpyrrolidone/vinylacetate copolymer, non-ionic polymer | 0.2% |
| 8 | LUVISKOL Plus | Polyvinylcaprolactam, non-ionic polymer | 0.5% |
| 9 | MOWIOL 18-88 | Polyvinyl Alcohol, non-ionic polymer | 0.2% |
| 10 | PLURACARE F127 | Ethylene oxide/propylene oxide copolymer, non-ionic polymer | 0.2% |
| 11 | SENSOMER 10M (Polyquaternium-10) | Polymeric quaternary ammonium derivative of hydroxyethyl cellulose, cationic polymer | 0.05% |
| 12 | SENSOMER JR 30M (Polyquaternium-10) | Polymeric quaternary ammonium derivative of hydroxyethyl cellulose, cationic polymer | 0.05% |
| 13 | UCARE JR 125 (Polyquaternium-10) | Polymeric quaternary ammonium derivative of hydroxyethyl cellulose, cationic polymer | 0.2% |
| 14 | UCARE JR 400 (Polyquaternium-10) | Polymeric quaternary ammonium derivative of hydroxyethyl cellulose, cationic polymer | 0.2% |
| 15 | SALCARE SC 95 (Polyquaternium-37) | Poly(2-methacryloxy-ethyltrimethylammonium chloride), cationic polymer | 0.2% |
| 16 | SALCARE SC 96 (Polyquaternium-37) | Poly(2-methacryloxy-ethyltrimethylammonium chloride), cationic polymer | 0.2% |
| 17 | MERQUAT 7SPR (Polyquaternium-7) | Poly(acrylamide-co-diallyldimethylammonium chloride), cationic polymer | 0.1% |
| 18 | MERQUAT 550PR (Polyquaternium-7) | Poly(acrylamide-co-diallyldimethylammonium chloride), cationic polymer | 0.2% |
| 19 | MERQUAT 2200 (Polyquaternium-7) | Poly(acrylamide-co-diallyldimethylammonium chloride), cationic polymer | 0.2% |
| 20 | CRODAFOS | Phosphate esters, non-ionic polymer | 0.4% |

TABLE 2-continued

| Sample | Adjuvant | Components of Adjuvant | Conc. Used |
|---|---|---|---|
| 21 | CRODAFOS + LUVISKOL K30 | Phosphate esters + Polyvinylpyrrolidone, non-ionic polymer | 0.125% + 0.075% |
| 22 | GELWHITE H | Anionic clay | 0.2% |
| 23 | GELWHITE GP | Anionic clay | 0.2% |
| 24 | GELWHITE H + S13 | Anionic clay + cationic polymer | 0.1% + 0.02% |
| 25 | GELWHITE GP + S3 | Anionic clay + cationic polymer | 0.075% + 0.2% |
| 26 | Xanthan Gum | Non-ionic polysaccharide | 0.1% |
| 27 | Sodium Carboxymethyl-cellulose (CMC) | Anionic cellulose | 0.1% |

EXAMPLE 4

Storage Tests of Silica Capsule Slurry Formulations with Surfactants and Polymers as Adjuvants To evaluate the storage stability of the capsules formulations described in Example 2, the samples were divided into two sets. One set was placed at room temperature and the other set was placed at 37° C. The samples were periodically examined for creaming and gelling. The amount of separation was measured and recorded after eight weeks. The results of this analysis are presented in Table 3.

TABLE 3

| Sample | Room Temp., 8 weeks | 37° C., 8 weeks |
|---|---|---|
| 1 | Flowable, trace separation | Flowable, trace separation |
| 2 | Separation and flowable, 8% water layer in bottom | Separation and flowable, 8% water layer in bottom |
| 3 | Separation and flowable, 15% water layer in bottom | Creamy and separation, 10% water layer in bottom |
| 4 | Separation, but flowable, 10% water layer in bottom separation | Separation, but flowable, 12% water layer in bottom separation |
| 5 | Separation with 3 layers, 10% loose cream on top, 18% water separation | Flowable, 10% loose cream on top, 10% water separation |
| 6 | Foaming and creamy | Creamy |
| 7 | Foaming, gel layer on top | Foaming, gel layer on top |
| 8 | Gel | Gel |
| 9 | Separation with 3 layers, flowable, 10% loose cream on top, 20% water separation | Separation with 3 layers, flowable, 10% loose cream on top, 25% water separation |
| 10 | Creamy and separation, 15% water layer in bottom | Creamy and separation, 5% water layer in bottom |
| 11 | Flowable, 2% water later in bottom, thin gel layer on top | Gel |
| 12 | Separation and flowable, 10% water layer in bottom | Creamy and separation, 12.5% water layer in bottom, thin gel layer |
| 13 | Flowable, 10% water layer in bottom | Creamy and separation, 10% water layer in bottom |
| 14 | Flowable, 4% water layer in bottom | Creamy and separation, 4% water layer in bottom |
| 15 | Flowable, 20% loose cream on top, 30% water separation | Creamy, 30% water separation in bottom layer |
| 16 | Flowable, 20% loose cream on top, 30% water separation | Creamy, 30% water separation in bottom layer |
| 17 | Flowable, 13% water separation | Creamy, 13% water separation in bottom layer |
| 18 | Gel | Cake |
| 19 | Flowable, 8% water separation | Gel |
| 20 | Creamy | Creamy |
| 21 | Creamy | Creamy |
| 22 | Flowable, 40% water separation | Creamy, 10% water separation |
| 23 | Flowable, 40% water separation | Creamy, 10% water separation |
| 24 | Flowable, 10% loose cream on top, 30% water separation | Creamy, 26% water separation |
| 25 | Flowable, 20% loose cream on top, 25% water layer in bottom | Creamy, 30% water separation |
| 26 | Xanthan Gum aggregates in slurry | Xanthan Gum aggregates in slurry |
| 27 | CMC aggregates in slurry | CMC aggregates in slurry |

This analysis indicated that adjuvants such as Polyquaternium-11, Polyquaternium-6, Polyquaternium-47, polyvinylpyrrolidone, and EO-PO polymers stabilized silica capsule slurries. For example, photographic images of the capsule slurry prepared with and without Polyquaternium-6 showed that there was no separation seen for the capsule slurry prepared with Polyquaternium-6, while samples prepared without Polyquaternium-6 displayed significant separation (FIG. 1).

The viscosity of Samples 1-3 was measured with a Brookfield DV-111 Ultra Programmable viscometer (Brookfield Engineering laboratories, Inc., Middleboro, Mass.). The results of this analysis are presented in Table 4.

TABLE 4

| Sample | Adjuvant | Viscosity (cP, Spindle RV5, 60 RPM) Room Temp., 8 weeks |
|---|---|---|
| 1 | LUVIQUAT PQ11 Polyquaternium-11 | 293 |
| 2 | MERQUAT 100 Polyquaternium-6 | 140 |
| 3 | MERQUAT 2001 Polyquaternium-47 | 1600 |

EXAMPLE 5

Sensory Performance of Stabilized Capsule Formulation

The sensory performance of adjuvant-stabilized silica capsule formulations in a roll-on base preparation (Table 5) was evaluated.

TABLE 5

| Ingredient | Amount |
|---|---|
| Water | to 100% |
| Aluminum Chlorohydrate or Aluminum Zirconium Tetrachlrohydrex Gly | 32-36% |
| Steareth-2, Stearth-20 | 0.5-4% |
| Silica | 1-5% |
| Glycerin | 3-5% |
| Dimethicone | 0.5 |

Panelists (30-35, with a mix of male and female) were instructed to shower with an unfragranced soap on the day of evaluation. For the comparative analysis, one underarm was applied with the test sample, the other with a control sample. The samples were composed of 0.35 g of roll-on base, pre-measured in a plastic syringe for easy application onto skin. Application of the samples was counterbalanced across underarms. Fragrance intensity was evaluated at 0, 8, 12 and 24 hours after application on a 0-10 intensity scale. Intensity ratings were entered by panelists into an automated data entry system, (COMPUSENSE at-hand) at the designated times. Intensity scores were averaged across panelists for each sample and analyzed by Two-Way ANOVA (p<0.1/90% CI).

Figure 2:
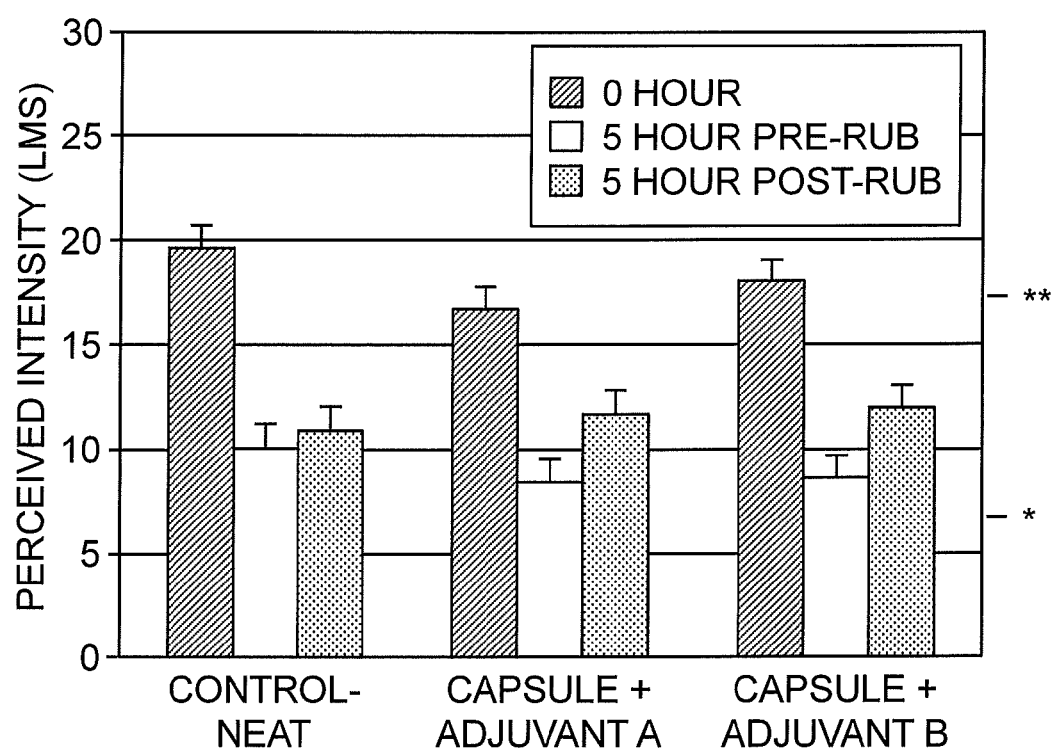
FIG. 2 shows the sensory performance of fragrance capsule slurries prepared with polymeric adjuvants in a roll-on base. Adjuvant A is Polyquaternium-11 (PQ-11) and Adjuvant B is Polyquaternium-6 (PQ-6). Fragrance is dosed at 0.5% neat oil equivalent in all samples. * weak, ** moderate.

The results of this analysis are presented in FIG. 2. It can be seen that the formulations containing the stabilized fragrance capsule slurry produced greater intensity after 5 hours compared with the formulation that only contained neat fragrance.

EXAMPLE 6

Clear Deodorant Stick Formulation

An exemplary clear deodorant stick formulation is provided in Table 6.

TABLE 6

| Ingredient | Percentage |
| --- | --- |
| Water | 20 |
| Phosphatidylglycerol/Diphosphatidylglycerol | 55 |
| Sodium Stearate | 6 |
| PEG-4 | 15 |
| Antibacterial Agent | 0.1 |

EXAMPLE 7

Antiperspirant Emulsion Spray Formulation

An exemplary antiperspirant emulsion spray formulation is provided in Table 7.

TABLE 7

| Ingredient | Percentage |
| --- | --- |
| Water | to 100 |
| Dimethicone | 6 |
| Aluminum Chlorohydrate | 5-6 |
| EDTA | 0.15 |
| Lauryl PEG-9 Polydimethylsiloxyethyl Dimethicone | 0.3 |
| Phenoxyethanol | 0.3 |
| Isobutane | 70 |

EXAMPLE 8

Antiperspirant Emulsion Roll-On Formulation

An exemplary antiperspirant emulsion roll-on formulation is provided in Table 8.

TABLE 8

| Ingredient | Percentage |
| --- | --- |
| Water | to 100 |
| Aluminum Chlorohydrate or Aluminum Zirconium Tetrachlorohydrex Gly | 32-36 |

TABLE 8-continued

| Ingredient | Percentage |
| --- | --- |
| Steareth-2, Steareth-20 | 0.5-4 |
| Silica | 1-5 |
| Glycerin | 3-5 |
| Dimethicone | 0.5 |

EXAMPLE 9

Antiperspirant Clear Emulsion Stick Formulation

An exemplary antiperspirant clear emulsion stick formulation is provided in Table 9.

TABLE 9

| Ingredient | Percentage |
| --- | --- |
| Water | 40 |
| Aluminum Zirconium Tetrachlorohydrex Gly | 20 |
| Stearyl Alcohol | 30 |
| C12-C15 Alkyl Benzoate | 25 |
| Glycine | 7 |
| Dimethicone | 0.07 |

EXAMPLE 10

Antiperspirant Opaque Emulsion Stick Formulation

An exemplary antiperspirant opaque emulsion stick formulation is provided in Table 10.

TABLE 10

| Ingredient | Percentage |
| --- | --- |
| Water | to 100 |
| Aluminum Chlorohydrate | 40 |
| Isopropyl Palmitate | 9 |
| Dimethicone | 5.8 |
| Synthetic Wax | 9 |
| Beheneth-10 | 2 |
| Polyglyceryl-3 Diisostearate | 0.3 |
| Acrylates Copolymer | 0.3 |
| PEG/PPG-18/18 Dimethicone | 2 |
| Phenoxyethanol | 0.5 |
| Pentylene Glycol | 0.5 |
| Cetyl PEG/PPG-10/1 Dimethicone | 2 |

EXAMPLE 11

Deodorant Spray Formulation

An exemplary deodorant spray formulation is provided in Table 11.

TABLE 11

| Ingredient | Percentage |
| --- | --- |
| Denatured Alcohol | 45 |
| Polyaminopropyl biguanide stearate | 0.2-0.5 |
| Butane, Isobutane, Propane, 152A | 55 |

EXAMPLE 12

Antiperspirant Clear Gel Formulation

An exemplary antiperspirant clear gel formulation is provided in Table 12.

TABLE 12

| Ingredient | Percentage |
| --- | --- |
| Water | 20 |
| Aluminum Zirconium Tetrachlorohydrex Gly | 25 |
| Silicone | 40 |
| Phosphatidylglycerol | 10 |
| Emulsifier | 10 |

What is claimed is:

1. A flowable, stable silica capsule formulation comprising a silica capsule suspension and an adjuvant, wherein the flowable, stable silica capsule formulation is flowable and stable for 4 to 8 weeks without forming a cream, foam or gel, the silica capsule suspension contains cetyltrimethylammonium chloride and core-shell silica capsules encapsulating an active material, the active material is a fragrance oil, and the adjuvant, present at a level of 0.05% to 0.5% by weight of the capsule formulation, is a vinyl pyrrolidone/dimethylaminoethyl methacrylate copolymer.

2. The flowable, stable silica capsule formulation of claim 1, wherein the active material is present at a level of 5% to 60% by weight of the capsule formulation.

3. The flowable, stable silica capsule formulation of claim 1, wherein the vinyl pyrrolidone/dimethylaminoethyl methacrylate copolymer is Polyquaternium-11.

4. The flowable, stable silica capsule formulation of claim 1, wherein the adjuvant is added to the silica capsule suspension during the preparation of the silica capsule suspension.

5. The flowable, stable silica capsule formulation of claim 1, wherein the adjuvant is added to the silica capsule suspension after the preparation of the silica capsule suspension.

6. A personal care product comprising the flowable, stable silica capsule formulation of claim 1.

7. The personal care product of claim 6, wherein said product is an aerosol antiperspirant, stick antiperspirant, roll-on antiperspirant, emulsion spray antiperspirant, clear emulsion stick antiperspirant, soft solid antiperspirant, emulsion roll-on antiperspirant, clear emulsion stick antiperspirant, opaque emulsion stick antiperspirant, clear gel antiperspirant, clear stick deodorant or spray deodorant.

8. The personal care product of claim 6, wherein said product is a shampoo, hair conditioner, hair rinse, hair refresher, body wash or soap.

9. A beauty care product comprising the flowable, stable silica capsule formulation of claim 1.

10. The beauty care product of claim 9, wherein said product is a fine fragrance or Eau De Toilette product.

11. A fabric care product comprising the flowable, stable silica capsule formulation of claim 1.

12. The fabric care product of claim 11, wherein said product is a rinse conditioner, liquid detergent or powder detergent.

13. A home care product comprising the flowable, stable silica capsule formulation of claim 1.

14. The home care product of claim 13, wherein said product is an all-purpose cleaner or fabric refresher.

15. A personal hygiene product comprising the flowable, stable silica capsule formulation of claim 1.

16. The personal hygiene product of claim 15, wherein the product is a hand sanitizer.

17. An oral care product comprising the flowable, stable silica capsule formulation of claim 1.

18. The oral care product of claim 17, wherein the product is a tooth powder.

* * * * *